United States Patent [19]

Trahey et al.

[11] Patent Number: 5,487,387
[45] Date of Patent: Jan. 30, 1996

[54] METHOD AND APPARATUS FOR DISTINGUISHING BETWEEN SOLID MASSES AND FLUID-FILLED CYSTS

[75] Inventors: Gregg E. Trahey, Hillsborough; Phyllis Kornguth, Durham; Kathryn Nightingale, Durham; William F. Walker, Durham, all of N.C.

[73] Assignee: Duke University, Durham, N.C.

[21] Appl. No.: 254,278

[22] Filed: Jun. 3, 1994

[51] Int. Cl.⁶ .................................................. A61B 8/00
[52] U.S. Cl. ........................ 128/660.02; 128/915
[58] Field of Search ................ 128/660.01, 660.02, 128/660.04, 660.05, 660.06, 660.07, 915; 73/599, 597, 618, 631

[56] References Cited

U.S. PATENT DOCUMENTS

| | | |
|---|---|---|
| 4,511,984 | 4/1985 | Sumino et al. |
| 4,733,668 | 3/1988 | Torrence ............................ 128/660.06 |
| 4,932,414 | 6/1990 | Coleman et al. |
| 5,007,428 | 4/1991 | Watmough ......................... 128/660.04 |
| 5,081,994 | 1/1992 | Hassler. |
| 5,086,775 | 2/1992 | Parker et al. |
| 5,099,848 | 3/1992 | Parker et al. |
| 5,109,857 | 5/1992 | Roundhill et al. |
| 5,211,169 | 5/1993 | Freeland. |

OTHER PUBLICATIONS

O. T. Von Ram and S. W. Smith; Beam Steering with Linear Arrays; *IEEE Transaction on Biomedical Engineering DME 30*; pp. 438–452 (1983).

T. A. Krouskop et al; A pulsed Doppler ultrasonic system for making noninvasive measurements of the mechanical properties of soft tissue; *Journal of Rehabilitation Research 24*, pp. 1–8 (1987).

B. A. Carroll and O. T. von Ramm; Fundamentals of Current Doppler Technology; *Ultrasound Quarterly 6*; pp. 275–298 (1988).

H. C. Starritt et al; An Experimental Investigation of Streaming in Pulsed Diagnostic Ultrasound Beams; *Ultrasound in Med & Biol 15*; pp. 363–373 (1989).

E. B. Mendelson, Ultrasound secures place in breast Ca management; *Diagnostic Imaging*, pp. 120–129 (1991).

A. T. Stavros and M. A. Dennis; The Ultrasound of Breast Pathology; *Percutaneous Breast Biopsy*; pp. 111–115 (1993).

*Primary Examiner*—George Manuel
*Attorney, Agent, or Firm*—Bell, Seltzer, Park & Gibson

[57] ABSTRACT

A method and apparatus for distinguishing between solid masses and fluid-filled cysts by using an ultrasonic transducer to transmit a plurality of ultrasonic signals into a target lesion within a human body and for receiving a plurality of reflected signals therefrom. At least one of the plurality of transmitting signals should be of sufficient intensity to initiate movement of any fluid located within the target lesion. A plurality of reflected ultrasonic signals are received from the target lesion and a comparison of differences between individual ones of the plurality of reflected signals is made to detect the presence or absence of fluid movement within the target lesion. Then a determination is made as to whether the target lesion is a fluid-filled cyst or a solid mass based upon the presence or absence of fluid within the target lesion.

57 Claims, 3 Drawing Sheets

▨ AREA OF MOVEMENT AWAY
▨ AREA OF MOVEMENT TOWARDS
▨ AREA OF NON-MOVEMENT

METHOD AND APPARATUS FOR DISTINGUISHING BETWEEN SOLID MASSES AND FLUID-FILLED CYSTS

FIELD OF THE INVENTION

The invention relates to the use of ultrasound in general, and more particularly to a method and apparatus for ultrasonically distinguishing between solid masses and fluid-filled cysts.

BACKGROUND OF THE INVENTION

The early detection of cancer has been of foremost concern to clinicians since the advent of the disease. All manner of methods have been applied to the detection or diagnosis from non-invasive to highly invasive. Noninvasive techniques, if effective, are preferred because of the decreased risk to the patient and the decrease in the associated costs.

As with most types of cancer, breast cancer patients benefit from early detection by realizing an increased survival rate. Mammography, a noninvasive technique is currently the foremost method of screening for breast cancer. Mammography has recently been supplemented by the use of ultrasound when evaluation of lesions identified in the mammographic diagnosis is uncertain. (Mendelson, Ellen B. *Ultrasound secures place in breast Ca management*, Diagnostic Imaging, April 1991, pp 120–129, 157). The use of ultrasound has in the past been limited to searching for the three accepted characteristics of fluid-filled cysts (i) a smooth exterior boundary; (ii) posterior enhancement; and (iii) weak internal echoes or anechoic. (Jackson, V. P., *The Role of US in Breast Imaging*, Radiology, 177: pp 305–311, 1990). If any of these characteristics is missing or cannot be clearly detected by the ultrasound, because the lesion contains cellular debris or is too small, it is common to perform a biopsy to conclusively determine whether the lesion is a solid mass which is possibly malignant or whether the lesion is merely a fluid-filled cyst.

However, despite the desire to use ultrasound, because of its safety, easy of use and low cost, current techniques are not very reliable in conclusively identifying the above-referenced characteristics of fluid-filled cysts. As a result, it is often still necessary to perform a biopsy to distinguish between a solid mass and a fluid-filled cyst.

The recent development of color flow Doppler has lead to a great deal of research being performed in the area of velocity detection in various organs or systems in the human body (Eyer et al. *Color Digital Echo/Doppler Image Presentation*, Ultrasound in Med. & Biol., Vol. 7, pp 21–33). For example, two popular areas of velocity detection research include the circulatory system (U.S. Pat. No. 5,109, 857 assigned to Applicant) and blood pool analysis in the heart (U.S. Pat. No. 5,211,169 to Freeland). Such techniques use a color video to represent the image which is generated by the ultrasound transducer. The movement of a fluid, for example blood, toward the transducer can be represented by red, an arbitrarily selected color. The movement of fluid away from the transducer has commonly been represented by blue, another arbitrarily selected color. Stationary objects are represented by shades of grey, with lighter shades of gray indicating more strongly reflecting objects.

A focus of current ultrasound research is the use of color flow Doppler, in the context of breast cancer diagnosis, to determine if a blood flow exists once a lesion has been determined, by means of the above-referenced diagnostic techniques. The existence of specific types of blood flow in a solid lesion is considered by some to be indicative of a cancerous tumor.

Ultrasound is a sound pressure wave which has in the past been used exclusively to sense the structure of tissue or to sense motion. Simply stated, ultrasound has been a means of passively measuring or sensing both the structure of tissue and the presence or absence of fluid motion. To date, applicant is unaware of any research or testing which has been performed to use an ultrasound device to actively induce movement of fluid within a lesion within the human body. The purpose for doing so would be to distinguish between a fluid-filled cyst and a solid mass to supplement mammography or to conduct an initial screening for lesions independent of mammography. The use of ultrasound would be a very valuable, safe, noninvasive and cost effective method of determining the nature of any lesions located during screening for breast cancer. In addition, such a technique would greatly reduce the number of unnecessary biopsies which are required because of the inability of current ultrasound techniques to conclusively determine if a lesion is solid or fluid-filled.

In addition to the above-mentioned medical uses, ultrasound is currently being used in a wide range of industrial applications. These include, for example, the inspection of steel plates, aircraft wings, turbine blades, ball bearings, and in flow measurements of gas and coal pipelines. Ultrasound is also used to monitor the curing of cheese and the status of cell cultures in bioreactors. In both of the latter applications, a device which can noninvasively distinguish between the solid and liquid states of a material would be beneficial. For example in cheese-making, the ability to determine the liquidity or solidity of a cheese wheel's core without cutting into it would save money and time. In a bioreactor, the ability to remotely monitor the clumping or gelling of cellular material would also be advantageous.

SUMMARY OF THE INVENTION

In view of the foregoing background, it is therefore an object of the present invention to provide a method of ultrasonically distinguishing between solid masses and fluid-filled cysts. The first step of the method is to transmit a plurality of ultrasonic signals into a target lesion located within a human body. At least one of the plurality of transmitting signals is preferably of sufficient intensity to initiate movement of any fluid which may be located within the target lesion. A plurality of reflected ultrasonic signals are then received from the target lesion and a comparison is made of the differences between individual ones of the plurality of the reflected signals to detect the presence or absence of fluid movement within the target lesion. A determination is made as to whether the target lesion is a fluid-filled cyst or a solid mass based upon the presence or absence of fluid movement within the target lesion.

A further object of the invention is to generate an image based upon quantitatively analyzing differences in time of arrival of each of the plurality of reflected signals, such that at least one of the reflected signals is used as a control against which subsequent reflected signals can be compared. Preferably, the image which is displayed is a color image based upon the difference in time of arrival between the plurality of reflected signals, wherein a longer period of time is represented by a first color, a shorter period of time is represented by a second color and no difference in time of arrival is represented by a third color. Alternatively, it may be beneficial to display a ratio representative of the magnitude of fluid movement away from a pulse generating transmitting means relative to fluid movement toward the transmitting means. It is also advantageous to generate and display a chart or spectrogram representative of the quantitative differences in time of arrival between the plurality of reflected signals.

An advantage of the present invention is the ability to determine if an identified lesion is a fluid-filled cyst or a solid mass, thereby reducing the need for the number of biopsies currently necessary under existing diagnostic techniques.

To perform the preferred technique for distinguishing between solid masses and fluid-filled cysts, it is beneficial to use an ultrasonic transducer to transmit a plurality of ultrasonic signals into a target lesion within a human body and to receive a plurality of reflected signals therefrom. It is advantageous to have at least one of the plurality of transmitting signals be of sufficient intensity to initiate movement of any fluid located within the target lesion. A storing means may also be provided for storing information from each of the plurality of reflected signals. Comparing means operatively associated with the storing means is used for comparing differences between individual ones of the plurality of reflected signals to detect the presence or absence of fluid movement within the target lesion. It is beneficial to provide means for determining whether the target lesion is a fluid-filled cyst or a solid mass is based upon the presence or absence of fluid within the target lesion is provided.

An advantage of the present invention is that this device may be used to distinguish between a solid tumor and a fluid-filled cyst in a breast of a subject, wherein the subject has not previously been diagnosed with a solid breast tumor.

A feature of the present invention is that a single transducer may be used to transmit a plurality of transmitting signals and receive a corresponding plurality of reflected signals. It is beneficial to have the transmitting signals be temporally spaced, such that each transmitting signal has a narrow beam width which is directed along a desired line of the target lesion and which is focused into a desired region of the target lesion.

A further object of the present invention is to use the radiation force phenomenon to induce acoustic streaming of any fluid in a lesion or material, and then detect any fluid motion using Doppler or other fluid motion techniques.

Still another object of the present invention is to provide an alternative embodiment of the invention which may be used for ultrasonically distinguishing between a solid state and a partially fluid state of a target material. A transducer is provided for transmitting a plurality of ultrasonic signals into the target material, wherein at least one of the plurality of transmitting signals is of sufficient intensity to initiate movement of any fluid located within the target material. It is beneficial if the transducer also receives a plurality of reflected ultrasonic signals from the target material. A processor is provided for comparing differences between individual ones of the plurality of reflected signals to detect the presence or absence of fluid movement within the target material. Once the comparison has been made, the results are displayed for determining whether the target material is solid or partially fluid based upon the presence or absence of fluid movement within the target material.

A preferred method for making this ultrasonic distinction between a solid state and a partially fluid state of a target material is to transmit a plurality of ultrasonic signals into the target, wherein at least one of the plurality of transmitting signals is of sufficient intensity to initiate movement of any fluid located within the target material. The next step in the method is to receive a plurality of reflected ultrasonic signals from the target material and compare the differences between individual ones of the plurality of reflected signals to detect the presence or absence of fluid movement within the target material. Once the comparison has been made, it is benefical to determine whether the target material is solid or partially fluid based upon the presence or absence of fluid movement within the target material.

BRIEF DESCRIPTION OF THE INVENTION

Some of the objects, features and advantages of the present invention having been stated, others will appear as the description proceeds, when taken in conjunction with the accompanying drawings in which.

DETAILED DESCRIPTION OF THE PREFERRED EMBODIMENT

The present invention will now be described more fully hereinafter with reference to the accompanying drawings, in which the preferred embodiment of the invention is shown. This invention may, however, be embodied in different forms and should not be construed as limited to the embodiments set forth herein. Rather, the illustrative embodiments are provided so that this disclosure will be thorough and complete, and will fully convey the scope of the invention to those skilled in the art. Like numbers refer to like elements throughout.

The term "region" of the present is that area which is analyzed by the present invention to detect the movement of any fluid existing within the lesion. The region interrogated by the present invention may include biological tissue such as animal tissue which may include lesion tissue. The present invention is not limited to biological systems, but may also be applied to other areas such as industrial applications, where the region maybe within the actual material being tested.

The term "differences" as used herein, in the context of the comparisons to be made between the reflected signals, means any distinguishable feature or characteristic of the reflected signal that is quantifiable. Examples of differences which may be compared include, but are not limited to; the time of arrival of a signal, phase, amplitude, and the intensity of a signal.

The term "time of arrival" refers herein to the measured elapsed time between the transmission of a transmitting signal and the return of a corresponding reflected signal. The time of arrival is measured by conventional measurement techniques.

As used herein, the term "high intensity" refers to an ultrasonic or acoustic pulse having a Spatial Peak Temporal Average of sufficient strength (a desired combination of (i) amplitude, (ii) pulse length, and (iii) pulse repetition frequency), to initiate fluid movement or acoustic streaming. Acoustic streaming relies upon the radiation force phenomenon which is associated with all forms of wave motion. The radiation force phenomenon is caused by a transfer of momentum from a wave to absorbing and reflecting obstacles in its path. When a wave propagates through a fluid, this momentum transfer generates a bulk steady motion of the fluid in the direction of wave propagation.

The term "low intensity" refers to an ultrasonic or acoustic pulse having a Spatial Peak Temporal Average of insufficient strength (a desired combination of (i) amplitude, (ii) pulse length, and (iii) pulse repetition frequency), to initiate fluid movement or acoustic streaming in the target lesion.

Figure 1:
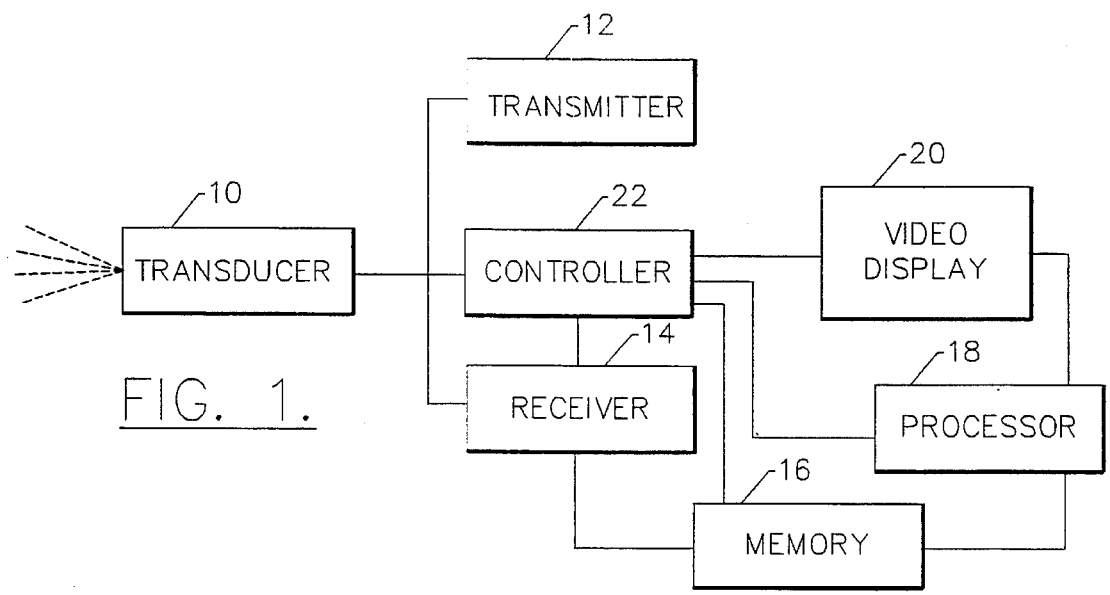
FIG. 1 is a schematic representation of the elements of the present invention.
Figure 2:
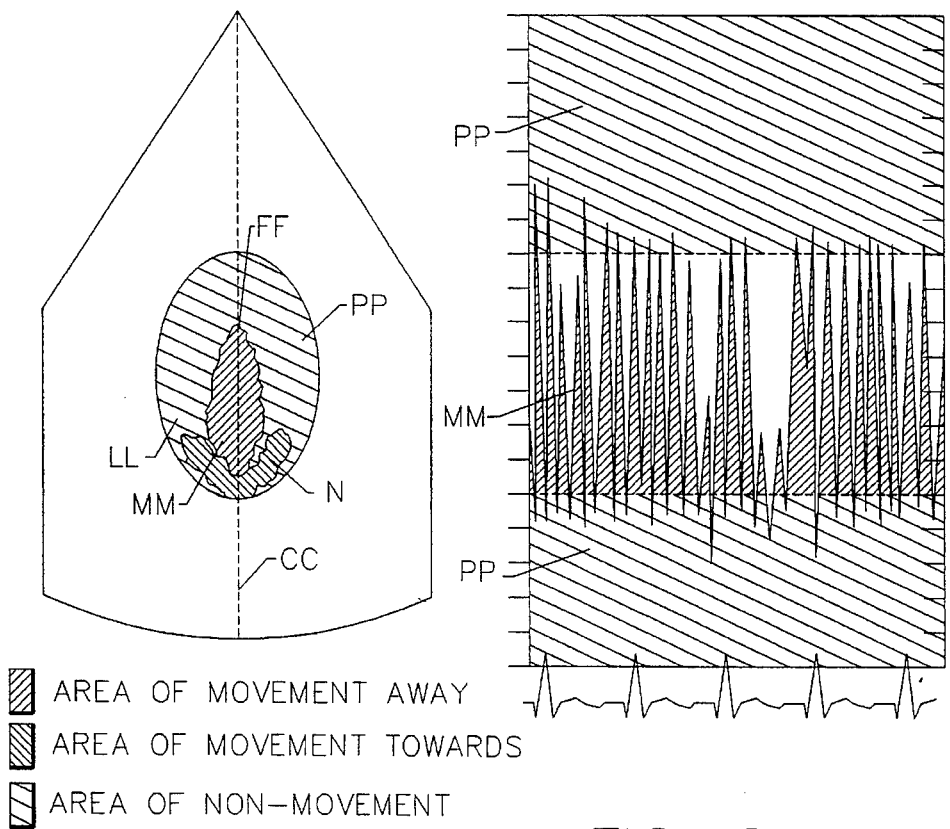
FIG. 2 is a view of the results obtained by the method depicted in FIG. 3, as seen on a video monitor.
Figure 3A:
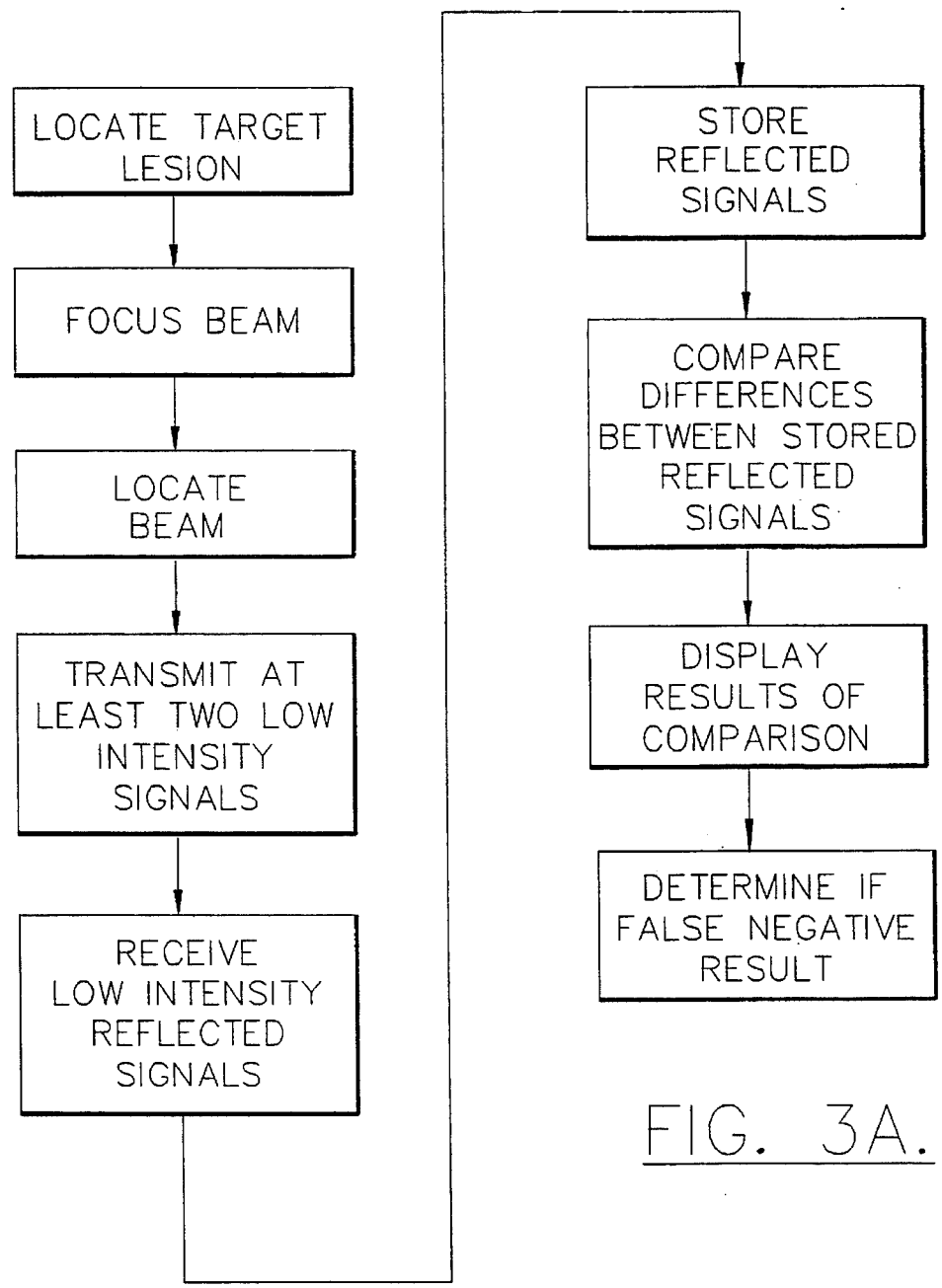
FIG. 3A is a flow chart showing the method steps of the initial setup and testing for false negative results.
Figure 3B:
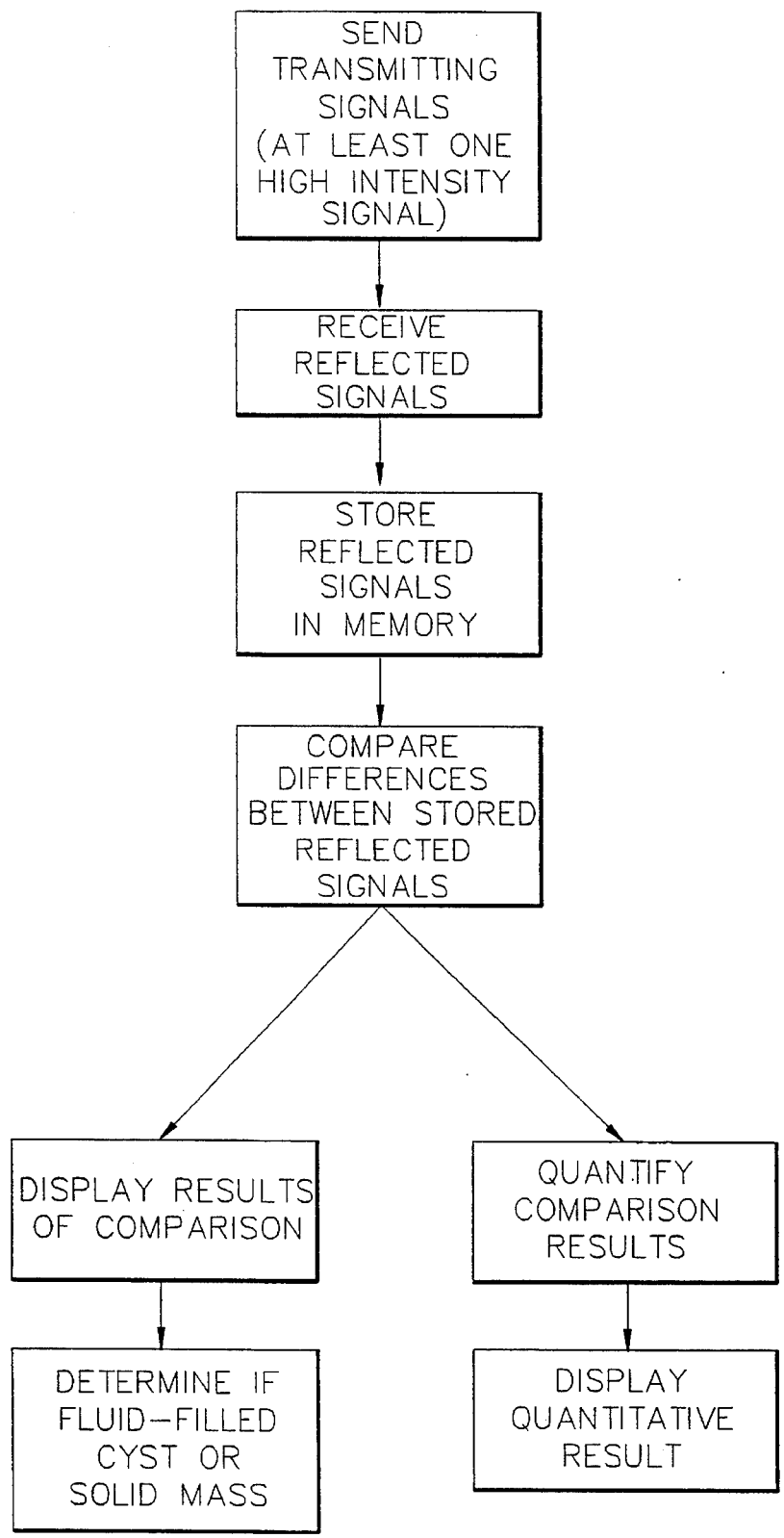
FIG. 3B is a flow chart showing the method steps of the present invention.

Referring now to the drawings, FIGS. 1 and 3A and 3B illustrate the specific apparatus and method of the present invention. As may be seen in FIG. 1, the elements of the present invention include a transducer 10, which has a transmitting function represented by a transmitter 12, and a receiving function represented by a receiver 14. The transducer 10 used in this embodiment of the invention is of the focused piezoelectric type manufactured by Siemens. As discussed in greater detail below, the transducer 10 is used to transmit an acoustic beam or pulse of energy (a transmitting signal) into the test region of the target lesion LL (shown in FIG. 2). A computer (not shown) is used which has a sufficient memory 16 to store information relating to each of the reflected signals. A processor 18 contained within the computer is used to compare, and in an alternative embodiment hereof, quantify the nature of the differences between the reflected signals. The results of this comparison are displayed on a video display 20 as shown in one form in FIG. 2. In an alternative embodiment (described in detail below) it is possible to display a quantitative ratio. Although not essential to the invention, it is possible to provide a controller 22 to control the timing and sequence of each of the events described above based upon desired parameters set by the operator.

FIG. 3A is directed to illustrating the preparation of the device and the method of conducting a preliminary test to avoid obtaining false negative results. Specifically, the transducer 10 is positioned or located within the target lesion LL and the beam emitted from the transducer is focused at the desired location within the lesion. In this embodiment, the focal point is set at location FF, as shown in FIG. 2. It is to be understood that this focal point may be varied as desired depending on the size, shape and nature of the lesion to be evaluated. The beam is also steered toward or located at the desired location within the target lesion LL. In this embodiment, the beam has been located at an approximate center line CC of the lesion LL.

It is the combination of the focal point FF and the location CC of the beam which determines the region to be evaluated. Alternative placement may be desirable in other lesions, for example if the lesion is very small it may be easier to initiate fluid movement by locating the beam adjacent an inside wall of the lesion.

Once it has been determined that the transducer 10 is focused and located in the desired position, the operator activates the transmitter 12 to have the transducer send at least two low intensity pulses into the lesion LL. The corresponding reflected pulses are received by the receiver 14 portion of the transducer 10. The information received by the receiver 14 is stored into the computer memory 16 and the differences between the reflected signals are compared by the processor 18. It is possible to use the first reflected signal as a control against which all subsequent reflected signals are compared. It is also possible to compare each subsequent reflected signal to its preceding reflected signal or use any combination thereof for purposes of comparison. The results of the comparison are displayed on the video display 22, in this embodiment a color monitor. From the display it is possible to determine that if any fluid movement exists as a result of the transmitted low intensity pulses it must be movement resulting from vascular flow. This step of transmitting and receiving low intensity signals is done to avoid obtaining a false negative result. Specifically, if this preliminary step is not performed, vascular blood flow, which is sometimes present in a cancerous tumor, may appear as acoustic streaming in the actual testing portion of this method and be misunderstood for a benign fluid-filled cyst.

FIG. 3B illustrates the remainder of the method of the present invention. The transmitter 12 is activated by the operator to transmit or send series of ultrasonic signals or pulses into a target lesion LL. In this embodiment the target lesion LL is located within a human body, and more specifically, within a lesion located within a human breast. At least one of the plurality of transmitting signals should be of the high intensity kind so as to initiate acoustic streaming of any fluid which may be located within the target lesion. The receiver 14 is also activated to receive a plurality of reflected ultrasonic signals from the target lesion. It is to be understood that in the present embodiment, the transmitting signals which are transmitted from the transducer 10 reflect off of the target lesion and are received by the transducer as reflected signals. It is also possible for the transducer 10 to transmit at least one high intensity signal to initiate acoustic flow of any fluid present in the lesion LL and then either consecutively or concurrently therewith, the transducer can transmit a series of low intensity signals which are to be received by the receiver 14 as the reflected signals. Therefore it is possible to use a separate (high intensity) transmitting signal to initiate acoustic streaming and separate (low intensity) detecting signals to be received as the reflected signals. Alternatively it is possible to use the same signals (high intensity) transmitted from the transducer to initiate acoustic streaming and be received as the reflected signals. Any combination or pattern of these transmitting and receiving functions of the transducer 10 may be used. For example, it is possible to send a transmitting signal and then receive the reflected signal or it is possible to send a series of transmitting signals and then receive a series of reflected signals. It is further possible to use a separate transducer for transmitting high intensity signals and a second transducer for transmitting and receiving low intensity signals.

Once the desired number of reflected signals have been received and stored in the memory 16 of the computer, it is possible for the processor 18 to compare the differences between individual ones of the plurality of reflected signals to detect the presence or absence of fluid movement with the target lesion. In the present embodiment, the comparison is done based upon the time of arrival of each of the individual reflected signals. If the time of arrival of a reflected signal is longer (ie., slower) than the time of arrival the reflected signal against which it is being compared, then acoustic streaming is occurring and fluid is moving away from the transducer 10, shown as MM in FIG. 2. If the time is shorter, then the fluid is moving toward the transducer 10, shown as NN in FIG. 2. The movement of fluid toward the transducer 10 may be caused by the fluid moving away MM from the transducer 10 and coming into contact with end of the lesion LL. If no movement or acoustic streaming is detected anywhere in the lesion LL, shown as PP in FIG. 2, then the lesion is considered to be a solid mass and a biopsy is indicated to determine if the lesion is malignant or benign.

Once this comparison has been performed, the processor converts the results into colors, one color representing movement away MM from the transducer 10 and a second color NN representing movement toward the transducer and a third color PP representing no movement, which are displayed on the video display 20 in the manner shown in FIG. 2. In an alternative embodiment (not shown) it is possible to display the results in the form of a chart or a spectrogram. In a further alternative embodiment, the processor conducts a further step of determining whether the proportion of fluid is moving toward or away from the transducer 10 and displays the results as quantitative ratio (not shown) rather than in the manner shown in FIG. 2. If the embodiment shown in FIG. 2 is used, then the operator must make a determination whether the target lesion is a fluid-filled cyst or a solid mass based upon the presence or absence of fluid movement within the target lesion.

This presence of fluid is determined by the nature and amount of color MM, NN, and PP which appear on the display and the location within the display of such color. In the B Mode with color flow overlay shown on the left hand side of FIG. 2, it may be seen that color MM appears along the center line CC of the beam beginning at the focal point FF thereof, which indicates that the high intensity beam transmitted by the transducer 10 caused acoustic streaming to occur. The fluid moving toward NN the transducer 10 is a result of contacting the end wall of the lesion LL. The remainder of the lesion LL does not show movement PP because it is not in the region of beam. The M mode displayed on the right hand side of FIG. 2 represents a repeated signal over time taken along the beam at line CC, which also shows acoustic streaming.

It is to be understood that the present invention may also be performed using other ultrasound motion detection techniques which are well known to those skilled in the art and remain within the spirit of the invention.

EXAMPLE 1

The tests were performed using a modified Siemens SI 1200 Ultrasonic Imaging Machine with variable acoustic pulse intensity. The center frequency of the transmitted pulses was 7.5 MHz. In this configuration, the machine has a fixed transmit focus, and the depth of maximum acoustic intensity is 2.6 cm in both Color-B Color-M mode (B/M/C mode) and Color M-Mode (M/C mode). These are the two modes that were used for this study. The Pulse Repetition Frequency (PRF) between Color-M pulses was 3.5 KHz. The transmitted acoustic intensity was controlled by modifying the pulse length of the Color-M mode pulses.

Acoustic intensities ranged from 0.6 to 4.4 W/cm² Spatial Peak Temporal Average ($I_{spta}$). Please note that all quoted $I_{spta}$ values refer to measurements made in water. The transducer was positioned so that the location of the maximum acoustic intensity of the pulse was inside the cyst. When necessary, this was accomplished using a non-attenuative standoff.

Intensity measurements were made using a PVDF membrane hydrophone (Sonic Technologies) in accordance with AIUM/NEMA Standards Publication/No. UL 1-1981. Spatial Peak Temporal Average and Spatial Peak Pulse Average ($I_{sppa}$) measurements were taken for varying pulse lengths in both M/C and B/M/C mode.

The patient sat in a chair and rested her breast on a table. The physician located the cyst using conventional B-Mode ultrasound, and then supported her arm in order to remain stationary during the examination. Stability of the breast and transducer throughout the insonification process was important to the success of this technique.

The machine was put into simultaneous B/M/C mode. The intensity of the Color M-Mode pulses was increased to a value of 1.56 W/cm² ($I_{spta}$). High intensity insonification lasted no more than ten seconds. During that time, the Color M-Mode display was observed to determine if motion has occurred in the cyst fluid. The patient was told to stop the experiment at any time if she felt any discomfort or heating.

The patient was then asked to palpate the cyst in order to agitate the cyst fluid, and the insonification procedure was repeated. Whenever flow was detected, the experiment was repeated with lower intensity pulses in order to establish a minimum intensity required to generate detectable acoustic streaming.

Seven women were studied, each of whom had a mammographic mass shown to be a cyst by conventional ultrasound examination. Cyst diameters ranged from 0.6 to 2.5 cm, and cyst depths were between 0.2 and 1.75 cm.

Table 1 below, summarizes the results of this study.

TABLE 1

| Patient | Cyst Diameter (cm) | Cyst Depth (cm) | $I_{spta}$ | Motion Type (W/cm²) |
|---|---|---|---|---|
| 1 | 1.55 | 1.75 | 1.56 | Intermittent |
| 2 | 2.05 | 1.0 | 1.43 | Steady |
| 3 | 0.83 | 0.75 | — | None |
| 4 | 1.5 | 0.5 | 1.43 | Intermittent |
| 5 | 2.5 | 1.2 | 1.56 | Intermittent |
| 6 | 0.59 | 0.2 | 1.43 | Steady |
| 7 | 0.96 | 1.1 | 1.43 | Steady |

Motion was successfully generated and detected in six of the seven cysts. In three cysts, clearly discernible, steady and/or high velocity motion (>3 cm/s) was detected. The fastest, most steady velocities were obtained in the cyst of patient number two. This cyst was 2.0 cm in diameter. It was located at a depth of 1 cm, thus the center of the lesion was near the maximum acoustic intensity of the beam. Motion did not occur for an $I_{spta}$ of 1.56 W/cm² until the patient palpated the cyst. Then motion began within 500 msec of high intensity insonification, and it remained steady for the entire ten seconds. Once streaming had occurred at this $I_{spta}$, it also occurred at an $I_{spta}$ of 1.43 W/cm². This cyst was diagnosed as a simple cyst.

Patient 6 had a 0.59 cm diameter cyst, at a depth of 0.2 cm, diagnosed to be a simple cyst. A standoff was used to position the peak acoustic intensity inside the cyst. The motion detected in this cyst was intermittent, however, the velocities of the detected motion were the fastest that were obtained during this study, between 3 and 4 cm/s at an $I_{spta}$ of 1.43 W/cm².

Patient 7 had a 0.96 cm diameter cyst located at a depth of 1.1 cm, diagnosed to be a simple cyst. The insonification process was performed on this patient with and without a standoff. Without a standoff, no motion was detected until the cyst was palpated and the $I_{spta}$ was raised to 4.4 W/cm². Once the standoff was put in place, locating the point of peak intensity inside the cyst, steady motion was detected at an $I_{spta}$ of 4.4 W/cm² and intermittent motion was detected at an $I_{spta}$ of 1.43 W/cm².

In three cysts intermittent, unsteady, lower velocity motion was detected. This motion was distinguishable from noise because when it was detected, it was located inside of the cyst and was in a direction predominantly away from the transducer. The diameters of these cysts ranged from 1.5 to 2.5 cm, and their depths ranged from 0.5 to 1.75 cm. Each of these cysts were diagnosed to be simple cysts.

In one case, no motion was detected. This was patient number 3. The cyst was 0.83 cm in diameter, and was located 0.75 cm from the surface of the tissue. At the time of this trial, the use of a standoff had not been indicated. This cyst was diagnosed to be "suggestive of a septated cyst".

The first patient reported slight heating during insonification with an $I_{spta}$ of 1.56 W/cm$^2$. No other patients reported heating.

In all cases that exhibited flow, palpation of the cyst enhanced streaming. This indicates an initial resistance to flow in the cyst fluid probably due to settling of the particulate matter in the cyst. Palpation agitates the cyst fluid thus reducing its resistance to streaming.

In two cases, an $I_{spta}$ of 1.56 W/cm$^2$ was required to induce detectable streaming. In four cases an $I_{spta}$ of 1.43 W/cm$^2$ was required. Below an $I_{spta}$ of 1.43 W/cm$^2$, no streaming was detected.

In the two cases when a standoff was used, higher velocity and or steady motion was detected. This can be attributed to two facts. The first is that the standoff positioned the point of peak intensity inside the cyst. The second is that the standoff is non-attenuative, therefore the peak intensity that reached these two cysts was greater than it was for the cysts that were located farther beneath the surface of the tissue.

The present invention may also be used in testing of other biological tissue. For instance, the above-described apparatus and method may be used to analyze lesions in other parts of the body such as the liver, the kidney, and the thyroid gland. It is possible to perform the above described techniques to determine whether a lesion in the kidney is either a solid mass or a fluid-filled cyst. Such a determination is medically significant for the same reasons presented in the context of breast cancer diagnosis and screening.

In addition, the present invention may also be used for industrial applications. For example, food products such as cheese can be evaluated to determine if they require additional curing or aging, which is indicated by acoustic streaming caused by the core of the cheese wheel being partially fluid verses a solid core representing a properly aged cheese wheel. A similar analysis is also possible in other industrial areas such as in a bioreactor where the clumping or gelling of cellular material can be tested using the above-described apparatus and techniques.

Many modifications and other embodiments of the invention will come to mind in one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

What is claimed is:

1. A method of ultrasonically distinguishing between solid masses and fluid-filled cysts, said method comprising:

transmitting a plurality of ultrasonic transmitting signals into a target lesion located within a human body, wherein at least one of said plurality of transmitting signals is of sufficient intensity to initiate movement of any fluid located within the target lesion;

receiving a plurality of reflected ultrasonic signals from the target lesion;

comparing differences between individual ones of said plurality of reflected signals to detect the presence or absence of fluid movement within the target lesion; and determining whether the target lesion is a fluid-filled cyst or a solid mass based upon the presence or absence of fluid movement within the target lesion.

2. A method according to claim 1 wherein said transmitting step comprises transmitting a series of temporally spaced signals.

3. A method according to claim 2 wherein said transmitting step further comprises the step of transmitting each of said plurality of signals with a narrow beam width.

4. A method according to claim 1 further comprises the step of directing said plurality of transmitting signals along a desired line of the target lesion.

5. A method according to claim 1 further comprises the step of focusing said plurality of transmitting signals into a desired region of the target lesion.

6. A method according to claim 1 further comprises the step of storing into memory at least two of said plurality of reflected signals received.

7. A method according to claim 1 wherein said comparing step comprises analyzing differences in time of arrival of each of said plurality of reflected signals, such that at least one of said plurality of reflected signals is used as a control against which subsequent reflected signals are compared.

8. A method according to claim 7 further comprising the step of generating a image based upon the differences between said plurality of reflected signals.

9. A method according to claim 8 wherein said generating step comprises displaying a color image based upon the difference in time of arrival between said plurality of reflected signals, wherein a longer period of time is represented by a first color, a shorter period of time is represented by a second color and no difference in time of arrival is represented by a third color.

10. A method according to claim 8 wherein said generating step comprises generating a chart representative of the quantitative differences in time of arrival between said plurality of reflected signals.

11. A method according to claim 1 wherein said receiving step comprises receiving at least one high intensity reflected signal.

12. A method according to claim 1 wherein said receiving step comprises receiving low intensity reflected signals.

13. An apparatus for ultrasonically distinguishing between solid masses and fluid-filled cysts, said apparatus comprising:

an ultrasonic transducer for transmitting a plurality of ultrasonic transmitting signals into a target lesion within a human body and for receiving a plurality of reflected signals therefrom, wherein at least one of said plurality of transmitting signals is of sufficient intensity to initiate movement of any fluid located within the target lesion;

means for storing information from each of said plurality of reflected signals;

comparing means operatively associated with said storing means for comparing differences between individual ones of said plurality of reflected signals to detect the presence or absence of fluid movement within the target lesion; and means for determining whether the target lesion is a fluid-filled cyst or a solid mass based upon the presence or absence of fluid movement within the target lesion.

14. An apparatus according to claim 13 further comprising display means for displaying an image representative of the differences between said plurality of reflected signals.

15. An apparatus according to claim 13 wherein said plurality of transmitting signals comprises a plurality of temporally spaced pulses.

16. An apparatus according to claim 13 wherein each of said plurality of transmitting signals comprises a narrow beam width.

17. An apparatus according to claim 13 wherein each of said plurality of transmitting signals comprises a pulse directed along a desired line of the target lesion.

18. An apparatus according to claim 13 wherein each of said plurality of transmitting signals comprises a pulse focused into a desired region of the target lesion.

19. An apparatus according to claim 13 wherein said comparing means comprises a processor for comparing differences in time of arrival of each of said plurality of reflected signals.

20. An apparatus according to claim 13 wherein said generated image comprises a ratio representative of the magnitude of fluid movement away from said transducer relative to fluid movement toward said transducer.

21. An apparatus according to claim 13 wherein said transducer receives at least one high intensity reflected signal.

22. An apparatus according to claim 13 wherein said transducer receives low intensity reflected signals.

23. An apparatus for ultrasonically distinguishing between solid masses and fluid-filled cysts, said apparatus comprising:
  means for transmitting a plurality of ultrasonic signals into a target lesion located within a human body, wherein at least one of said plurality of transmitting signals is of sufficient intensity to initiate movement of any fluid located within the target lesion;
  means for receiving a plurality of reflected ultrasonic signals from the target lesion;
  means for comparing differences between individual ones of said plurality of reflected signals to detect the presence or absence of fluid movement within the target lesion; and
  means for determining whether the target lesion is a fluid-filled cyst or a solid mass based upon the presence or absence of fluid movement within the target lesion.

24. An apparatus according to claim 23 further comprising means for generating a image based upon the differences between said plurality of reflected signals.

25. An apparatus according to claim 23 wherein said transmitting means comprises a transducer.

26. An apparatus according to claim 23 wherein said receiving means comprises a transducer.

27. An apparatus according to claim 23 wherein said transmitting means and said receiving means comprise a single transducer.

28. An apparatus according to claim 27 wherein said transducer receives at least one high intensity reflected signal.

29. An apparatus according to claim 27 wherein said transducer receives low intensity reflected signals.

30. An apparatus according to claim 23 wherein said transmitting means comprises a transducer capable of transmitting a plurality of transmitting signals.

31. An apparatus according to claim 30 wherein each of said plurality of transmitting signals comprises temporally spaced pulses having a narrow beam width directed along a desired line of the target lesion.

32. An apparatus according to claim 30 wherein each of said plurality of transmitting signals comprises a pulse focused into a desired region of the target lesion.

33. An apparatus according to claim 23 wherein said comparing means comprises a processor for comparing differences in time of arrival of each of said plurality of reflected signals.

34. An apparatus according to claim 23 further comprising means for generating an image based upon the differences between said plurality of reflected signals.

35. An apparatus according to claim 34 wherein said generated image comprises a ratio representative of the magnitude of fluid movement away from a pulse generating transmitting means relative to fluid movement toward said transmitting means.

36. A method of ultrasonically distinguishing between a solid tumor and a fluid-filled cyst in a breast of a subject, wherein the subject has not previously been diagnosed with a solid breast tumor, said method comprising:
  transmitting a plurality of ultrasonic signals into a target tumor located within the breast of the subject, wherein at least one of said plurality of transmitting signals is of sufficient intensity to initiate movement of any fluid located within the target tumor;
  receiving a plurality of reflected ultrasonic signals from the target lesion;
  comparing differences in between individual ones of said plurality of reflected signals to detect the presence or absence of fluid movement within the target lesion; and
  determining whether the target lesion is a fluid-filled cyst or a solid mass based upon the presence or absence of fluid movement within the target lesion.

37. A method according to claim 36 further comprising the step of displaying a quantitative value representative of the direction of movement of any fluid within the target lesion based upon differences in time of arrival between said plurality of reflected signals.

38. A method according to claim 36 wherein said displaying step comprises displaying a ratio representative of the magnitude of fluid movement away from a signal generating transducer relative to fluid movement toward said transducer.

39. A method according to claim 36 wherein said comparing step comprises quantitatively analyzing differences in time of arrival of each of said series of reflected signals, such that a first reflected signal is used as a control against which a subsequent plurality of reflected signals are compared.

40. A method according to claim 36 further comprising the step of generating a image based upon the differences between said plurality of reflected signals.

41. A method according to claim 36 wherein said generating step comprises displaying a color image based upon the difference in time of arrival between said reflected signals, wherein a longer period of time is represented by a first color, a shorter period of time is represented by a second color and no difference in time of arrival is represented by a third color.

42. A method according to claim 36 wherein said generating step comprises generating a chart representative of the quantitative differences in time of arrival between said reflected signals.

43. A method according to claim 36 wherein said transmitting step comprises transmitting a series of temporally spaced pulses.

44. A method according to claim 36 wherein said transmitting step further comprises the step of transmitting a plurality of pulses, each of said pulses having a narrow beam width.

45. A method according to claim 36 further comprising the step of directing each of said transmitting signals along a desired line of the target lesion.

46. A method according to claim 36 further comprising the step of focusing each of said transmitting signals into a desired region of the target lesion.

47. A method according to claim 36 further comprising the step of storing into memory at least two of said plurality of reflected signals.

48. An apparatus for ultrasonically distinguishing between a solid state and a partially fluid state of a target material, said apparatus comprising:

means for transmitting a plurality of ultrasonic signals into the target material, wherein at least one of said plurality of transmitting signals is of sufficient intensity to initiate movement of any fluid located within the target material;

means for receiving a plurality of reflected ultrasonic signals from the target material;

means for comparing differences between individual ones of said plurality of reflected signals to detect the presence or absence of fluid movement within the target material; and means for determining whether the target material is solid or partially fluid based upon the presence or absence of fluid movement within the target material.

49. An apparatus according to claim 48 further comprising means for generating a image based upon the differences between said plurality of reflected signals.

50. An apparatus according to claim 48 wherein said transmitting means comprises a transducer.

51. An apparatus according to claim 48 wherein said receiving means comprises a transducer.

52. An apparatus according to claim 48 wherein said transmitting means and said receiving means comprise a single transducer.

53. An apparatus according to claim 52 wherein said transducer receives at least one high intensity reflected signal.

54. An apparatus according to claim 52 wherein said transducer receives low intensity reflected signals.

55. An apparatus according to claim 48 wherein said transmitting means comprises a transducer capable of transmitting a plurality of transmitting signals.

56. An apparatus according to claim 55 wherein each of said plurality of transmitting signals comprises temporally spaced pulses having a narrow beam width directed along a desired line of the target material.

57. An apparatus according to claim 55 wherein each of said plurality of transmitting signals comprises a pulse focused into a desired region of the target material.

* * * * *